United States Patent [19]
Rutnarak

[11] Patent Number: 4,624,667

[45] Date of Patent: Nov. 25, 1986

[54] ADDITIVE TRANSFER DEVICE

[75] Inventor: Sangvorn Rutnarak, Vernon Hills, Ill.

[73] Assignee: Abbott Laboratories, North Chicago, Ill.

[21] Appl. No.: 619,669

[22] Filed: Jun. 11, 1984

[51] Int. Cl.[4] .......... A61M 5/00; A61J 1/08

[52] U.S. Cl. .......... 604/414; 604/413; 604/111; 604/88

[58] Field of Search .......... 604/82, 86–88, 604/110–111, 244, 411, 414, 413, 201, 203, 204; 141/329–330

[56] References Cited

U.S. PATENT DOCUMENTS

| | | | |
|---|---|---|---|
| 3,563,373 | 2/1972 | Paulson | 604/88 |
| 3,826,261 | 7/1974 | Killinger | 604/414 |
| 3,908,654 | 9/1975 | Lhoest et al. | 604/88 |
| 3,938,520 | 2/1976 | Scislowicz et al. | 604/414 |
| 3,940,003 | 2/1976 | Larson | 604/411 |
| 3,977,555 | 8/1976 | Larson | 604/411 |
| 3,994,412 | 11/1976 | Difiglio | 604/111 |
| 4,180,070 | 12/1979 | Genese | 604/414 |
| 4,200,100 | 4/1980 | Willis | 604/414 |
| 4,328,802 | 5/1982 | Curley et al. | 604/88 |
| 4,334,536 | 6/1982 | Pfleger | 604/201 |
| 4,430,077 | 2/1984 | Mittleman et al. | 604/111 |
| 4,516,967 | 5/1985 | Kopfer | 604/87 |

FOREIGN PATENT DOCUMENTS 2538457 3/1976 Fed. Rep. of Germany ...... 604/415

*Primary Examiner*—Dalton L. Truluck
*Assistant Examiner*—Michelle N. Lester
*Attorney, Agent, or Firm*—Alan R. Thiele; Michael J. Roth; Martin L. Katz

[57] ABSTRACT

An improved additive transfer device for storing and subsequently transferring a fluid material from an additive container to a rigid or semirigid solution container having an exposed closure. The improved additive transfer device is mounted on the additive container and includes a closure assembly fabricated from three components; a pierceable stopper, a slidable piercing pin and a hood member. The closure assembly is adapted to be positioned on the solution container. The two ended slidable piercing pin is disposed in a central opening in the pierceable stopper so that one end will pierce a diaphragm contained in the pierceable stopper. Resistance elements are provided between the slidable piercing pin and the central opening in the pierceable stopper to hold the slidable piercing pin away from the diaphragm in the pierceable stopper in one position and allow the slidable piercing pin to pierce the diaphragm and retain it within the central opening in a second position.

20 Claims, 3 Drawing Figures

ADDITIVE TRANSFER DEVICE

BACKGROUND OF THE INVENTION

This invention relates to an improved device for transferring a fluid material to a solution container having an exposed closure. More particularly, this invention relates to an improved additive device wherein the closure assembly for the additive container is formed from three basic components; a pierceable stopper, a slidable piercing member and a hood element.

Transfer devices of the type concerned with in this invention are described in U.S. Pat. No. 3,987,791 (U.S. Pat. No. Re. 29,656); U.S. Pat. Nos. 4,020,839; 4,303,069; 4,334,536; and 3,788,369. In U.S. Pat. No. 3,987,791 a multi-component additive transfer unit is described, whereas in U.S. Pat. No. 4,020,839 a three-piece transfer unit is disclosed; however, it does not have a double pointed piercing member which can be sequentially positioned and retained by the stopper in an additive container. In U.S. Pat. No. 4,303,069 a multi-component piercing assembly is described which utilizes a bellows portion in conjunction with the piercing member, whereas in U.S. Pat. No. 4,334,536 a multi-breakaway syringe needle assembly is illustrated for a hypodermic syringe. In U.S. Pat. No. 3,788,369 a double-pointed transfer unit is illustrated for use in conjunction with a rigid vial and a flexible container.

Nowhere in the prior art is there available an additive transfer unit which is composed of a minimum number of parts, yet will permit the sterile transfer of a fluid component from an additive vial to a solution container. Neither does the prior art provide an additive transfer closure system which is adaptable for use with either a rigid, semirigid or flexible container, while affording a sterile and readily activated transfer of fluid material between containers.

It is an advantage of the present invention to afford an improved additive transfer device which is composed of a minimum number of parts. Other advantages are an improved additive transfer device which is adaptable to be utilized in conjunction with either a flexible, semirigid, or rigid vial; is readily activated, but can be maintained in a sterile condition until activation; offers the versatility of several types of sealing engagements between the covering hood member and the container; and can be manufactured without specialized tooling as well as assembled without expensive manufacturing procedures.

SUMMARY OF THE INVENTION

The foregoing advantages are accomplished and the shortcomings of the prior art are overcome by the present improved additive transfer device wherein the opening in an additive container for storing a fluid medicament is closed by a pierceable closure or stopper having a shoulder for resting against the finish of a substantially rigid neck of the additive container. The pierceable stopper has a guide channel for receiving a double-ended piercing member or piercing pin having a passageway therethrough for the flow of fluid material. The piercing pin has a point on either end and is slidably positioned within the guide channel in the pierceable stopper. First and second resistance means are operatively positioned with respect to the piercing pin in the guide channel to position one of the piercing pin points away from the pierceable stopper in one position and through the pierceable stopper in a second position. A hood member has a flange portion to sealably contact a shoulder on the pierceable stopper. Sealing means are positioned between the pierceable stopper and the additive container finish. In the preferred embodiment a diaphragm is positioned at one end of the guide channel in the pierceable stopper adjacent the additive container opening. In an alternate embodiment, the pierceable closure and the hood member include complementary and engagable threads, and the guide channel in the pierceable stopper is defined by an outwardly extending tubular member. In the preferred embodiment, the first and second resistance means are defined by spaced apart projections extending from the side of the piercing pin with at least one projecting member extending inwardly into the guide channel. In an alternate embodiment, a third resistance means is positioned with respect to the piercing pin and the guide channel to position one end of the piercing pin points away from the pierceable stopper. In another alternate embodiment, the hood member has a weakened portion so that it can be readily removed at the time of activation of the improved additive transfer device.

BRIEF DESCRIPTION OF THE DRAWINGS

A better understanding of the improved additive transfer device of this invention will be afforded by reference to the drawings, wherein.

DESCRIPTION OF THE EMBODIMENTS

Figure 1:
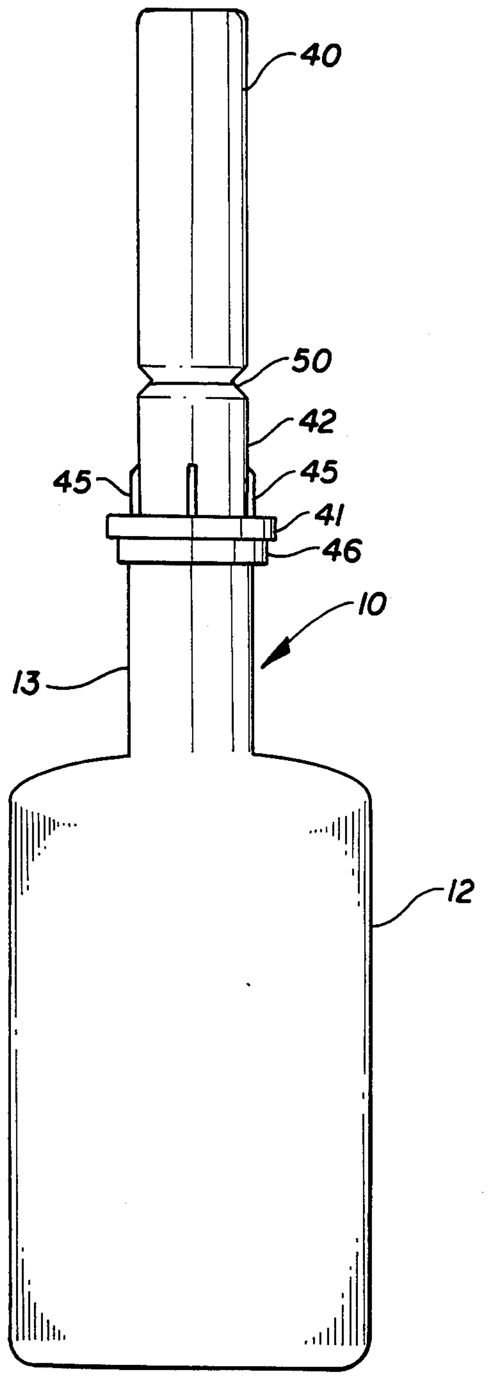
FIG. 1 is a view in front elevation illustrating one of the embodiments of this invention.
Figure 2:
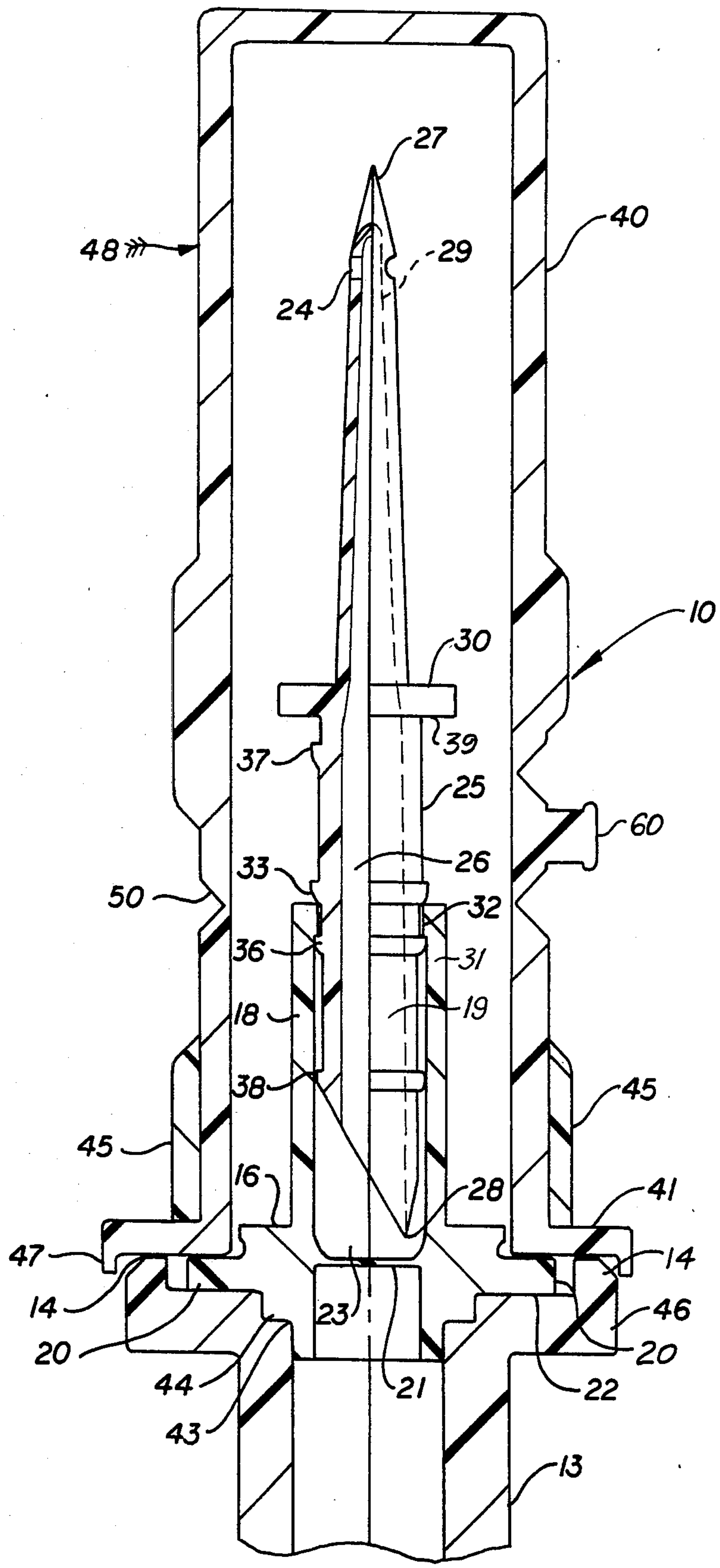
FIG. 2 is an enlarged view in vertical section illustrating the improved transfer device shown in FIG. 1.

Proceeding to a detailed description of one embodiment of the invention, the improved additive transfer device generally 10 is illustrated in FIGS. 1 and 2 and includes an additive container or vial 12 with a neck 13 terminating in a finish 14. A closure or stopper 16 has a shoulder 20 for resting upon shoulder portion or second finish 22 of mouth 46 of container 12. Stopper 16 includes a diaphragm section 21 at the inner end of tubular guide channel 18. Piercing pin 25 has a first portion 19 extending into guide channel 18. Piercing pin 25 is held in one position therein by means of inwardly extending annulus 32 on stopper 16 positioned between annular projections 33 and 36 on piercing pin 25. Annulus 32 may be positioned on the end of outwardly extending tubular member 31. Piercing pin 25 also includes projection 38 positioned adjacent piercing point 28 and projection 37 positioned adjacent flange 30. A passageway 26 extends longitudinally through piercing pin 25 terminating in orifices 24 and 29 adjacent piercing point 27. Stopper 16 has opening 23 in tubular guide channel 18 as well as a transverse portion 44 for complementary sealing and stating against transverse portion 43 in container mouth 46.

A hood element 40 covers piercing pin 25 as well as stopper 16. Hood element 40 has a flange 41 for contact with finish 14 on vial 12 seating against shoulder 20 of stopper 16. It will be noted that hood 40 has a weakened portion 50 in the form of a V-shaped groove or a tear strip 60 as well as support flanges 45.

Figure 3:
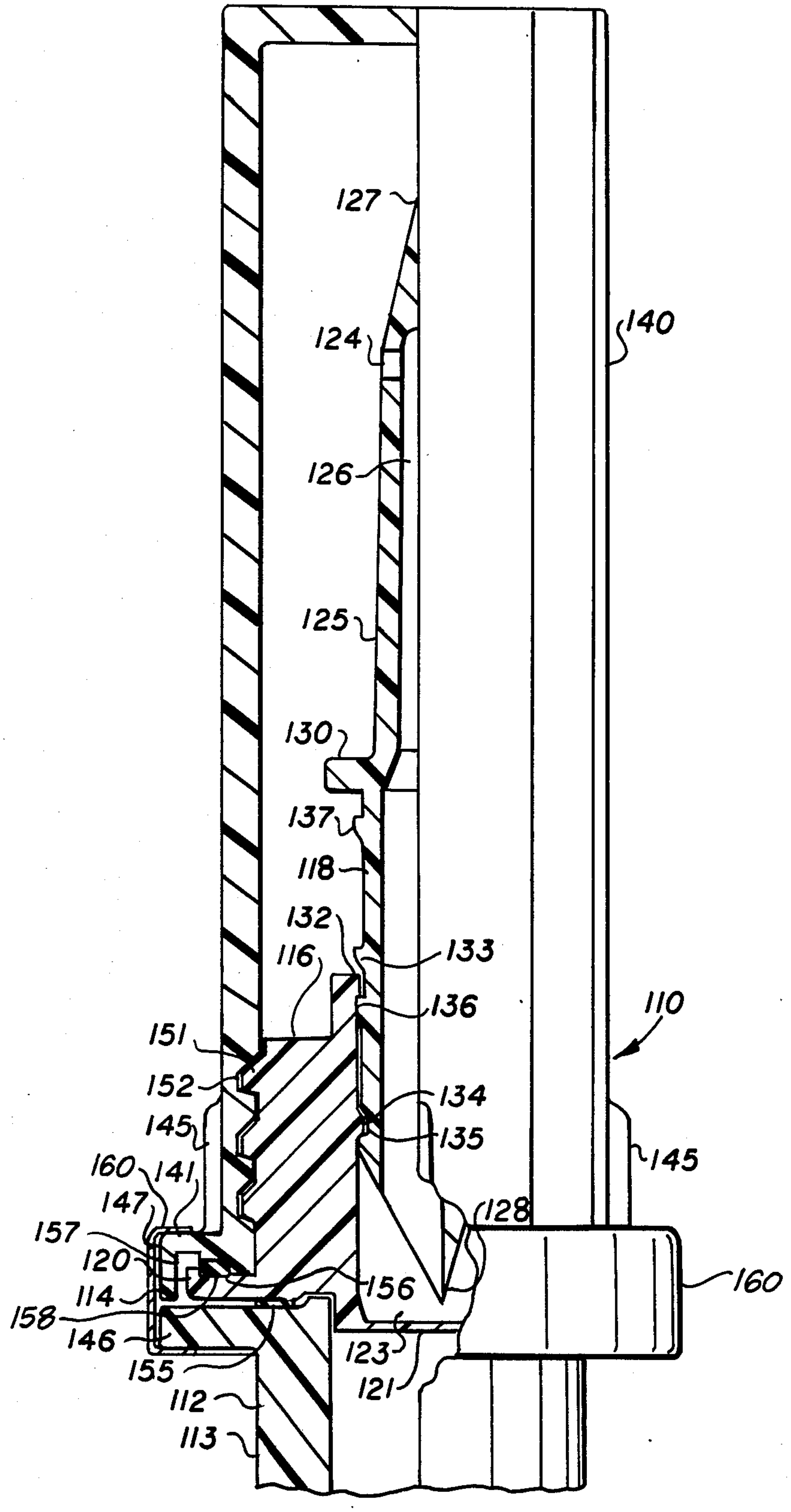
FIG. 3 is a view similar to FIG. 2 illustrating still another embodiment of this invention.

Referring to FIG. 3, an alternate embodiment generally 110 is therein described. The same or similar components are designated by the same numbers except they are referred to in the "100" series. The major difference between the two additive transfer units 10 and 110 is in the provision of complementary threads 151 and 152 for engagement between stopper 116 and hood member 140. Another difference between embodiments 10 and 110 is hood member 140, stopper 116 and mouth 146 of plastic container or vial 112. Hood member 140 also has a flange 141 extending laterally from the threaded area with a shorter flange 157 extending downwardly and transversely from flange 141. Flange 141 engages a seal ring 156 positioned in an accommodating groove 158 in shoulder 120 of stopper 116. An additional heat or spin weld seal 155 is formed between stopper 116 and finish 114. Another difference between stopper systems 10 and 110 is in place of one of the annular projections 33, 36 or 38 on piercing pin 25 (FIG. 2), a groove 135 is provided in piercing pin 125 and a projection 134 extends from stopper 116 to be accommodated therein. It will also be noted that in conjunction with additive transfer unit 110 that shorter flange 157 of hood 140 is coextensive with the outside edge of mouth 146. This is unlike the offset position of skirt 47 with respect to the edge of mouth 46 in unit 10 (FIG. 2). The coextensive position of shorter flange 157 and the outside edge of mouth 146 enables the addition of a tear-away seal or shrink wrap 160 for tamper indication and additional security.

Operation

A better understanding of the advantages of the improved additive transfer units 10 and 110 will be had by description of their operation. As the operation of unit 110 is substantially the same as that for unit 10, only the differences with respect to unit 110 in its operation will be described.

The assembly of improved additive transfer unit 10 is effected with a minimum number of steps. After the additive container 12 is filled and sterilized, stopper 16 will be positioned in mouth 46 with transverse portion 43 of stopper 16 and transverse portion 44 of finish 14 seated together. Piercing pin 25 will then be positioned axially in tubular guide channel 18 in the manner indicated in FIG. 2. As shown in the preferred embodiment inwardly extending annulus 32 on stopper 16 will be positioned between projections 33 and 36. It will be understood that additional appropriately positioned annuluses may be used. Subsequently, hood member 40 will be positioned over pin 25 with flange 41 in contact with shoulder 20 of stopper 16 as well as seated on finish 14. Flange 41 will be sealed to finish 14 and shoulder 20 by means of heat sealing or spin welding. Both mouth 46 and flange 41 are formed from a thermoplastic resinous material.

When it is desired to transfer the fluid material in additive vial 12 to a solution container (not shown) which can be of the flexible semirigid or rigid type, all that is required is to exert a lateral force on the upper portion of hood member 40 such as indicated by arrow 48. As hood member 40 is formed from a flexible plastic material this force will cause breaking at weakened portio 50. Hood member 40 may be removed when the break at weakened portion 50 extends completely around hood member 40. Access to piercing pin 25 is thereby obtained. Piercing pin 25 may now be moved axially toward container 12 in tubular guide channel 18. Movement of piercing pin 25 toward additive vial 12 is effected by first causing piercing point 27 to move through the stopper in a solution container similar to that identified by reference number 46 in U.S. Pat. No. 3,987,791. Axial force is then used to move piercing pin 25 so that annulus 32 overrides annular projection 33 and seats itself between projection 37 and the underside 39 of flange 30. This movement of piercing pin 25 will cause piercing point 28 to move through diaphragm section 21 of stopper 16. Fluid communication between the contents of container 12 and passageway 26 is thereby provided. When additive container 12 is made from a flexible material, squeezing of vial 12 will facilitate the movement of the contents of vial 12 into passageway 16.

The fabrication and operation of unit 110 is substantially the same as that for unit 10 except for the following differences. It will be noted that there is no weakened portion in hood member 140. Accordingly, hood member 140 will be removed by rotatably disengaging threads 152 from threads 151. This disengagement will cause preliminary breaking away of flange 141 from seal ring 156. Seal 156 will be positioned on shoulder 120 in accommodating groove 158. Hood member 140 will then be placed over stopper 116 by interengagement of threads 152 with threads 151. To operate unit 110, all that is required is rotatable disengagement of hood member 140 from stopper 116. Fluid communication between vial 112 and passageway 126 will be as previously described in conjunction with unit 10. Piercing pin 125 will be assisted in its positioning away from diaphragm 121 by the seating of projection 134 in groove 135 as well as the positioning of annulus 132 on stopper 116 between projections 133 and 136 on piercing pin 125.

An important feature of units 10 and 110 is their simplified construction. It will be noted that in each embodiment, a three-piece additive transfer unit unit is provided consisting of a stopper 16 or 116; piercing pins 25 or 125 and a hood member 40 or 140. This simplified construction is afforded in part by the unique manner in which stoppers 16 and 116 are seated upon and/or are sealed to the mouths of the respective additive containers 12 or 112. Additionally, in conjunction with additive transfer device 10, another advantage is its removable hood member 40 having either a weakened portion 50 or a tear strip 60 so that it can be quickly removed. Unauthorized tampering with the additive transfer device is indicated when weakened portion 50 or tear strip 60 do not form a contiguous ring around hood member 40.

The preferred use of vials 12 and 112 is with a fluid medicament material of the additive type which requires dilution before use. If desired the fluid medicament stored in vial 12 or 112 could be potassium chloride, lidocain or trace metals and the diluent material in the solution container might be a normal saline solution or water. It should be understood that the term "fluid medicament" or "fluid material" as employed in the specification and claims is meant to mean any medicament or diluent material which will flow from one container to another whether a liquid, solid or gas.

Hood members 40 and 140 are fabricated by using standard injection molding techniques and a polypropylene material. However, other materials such as a polyethylene, or a copolymer of polypropylene and polyethylene could be used. Similarly, stoppers 16 and 116 are fabricated by injection molding from a polypropylene material. However, other suitable materials which could be utilized are a polyethylene material or a copolymer of polypropylene or polyethylene. Piercing pins 25 and 125 are manufactured from a polycarbonate material by standard injection molding techniques. Other materials which could be utilized for piercing pin 25 are stainless steel with nylon, or polypropylene.

It will thus be seen that through the present invention there is now provided an improved additive transfer device employing a minimum number of parts, that can be readily activated in a quick and efficient manner. The improved additive transfer device of this invention is, by nature of its simplified construction, easily fabricated and has the versatility of affording either a breakaway or threaded cover member. Further, an improved additive transfer system is afforded which has the versatility of being utilized with different sealing techniques for use in conjunction either with a rigid, semirigid or flexible container neck.

The foregoing invention can now be practiced by those skilled in the art. Such skilled persons will know that the invention is not necessarily restricted to the particular embodiments presented herein. The scope of the invention is to be defined by the terms of the following claims as given meaning by the preceding description.

What is claimed is:

1. An improved additive transfer device for storing and transferring a fluid material to a solution container having an exposed stooper, comprising:

an additive container for storing the fluid material, said additive container having a substantially rigid neck portion defining a finsh and an opening therethrough;

a pierceable stopper having a shoulder for resting against said finish of said container neck and positioned to close said opening in the additive container, said pierceable stopper including a guide channel;

a piercing pin having a point on each end, and a passageway therethrough for the flow of the fluid material said piercing pin being slidably positioned within said guide channel;

first and second resistance means comprising spaced-apart projections extending from said piercing pin and at least one annulus extending into said guide channel to position one of said piercing pin points away from said pierceable stopper in one position and to permit passage of said piercing pin point through said pierceable stopper in another position;

a hood member having a flange portion to sealably contact said shoulder of said pierceable stopper; and sealing means positioned between said pierceable stopper and said container finish;

whereby a fluid pathway is provided between the containers to permit the fluid material within said additive container to be transferred onto the solution container when said piercing pin pierces said pierceable stopper.

2. The additive transfer device as defined in claim 1 wherein said pierceable stopper includes a diaphragm positioned at one end of said guide channel adjacent said container opening.

3. The additive transfer device as defined in claim 2 wherein said pierceable stopper and said hood member include complementary and engagable threads.

4. The additive transfer device as defined in claim 1 wherein said guide channel is defined by an outwardly extending tubular member.

5. The additive transfer device as defined in claim 1 wherein said piercing pin includes a flange extending from said piercing pin spaced from one of said projections on said piercing pin.

6. The additive transfer device as defined in claim 1 wherein said projections on said piercing pin are of a generally annular configuration.

7. The additive transfer device as defined in claim 6 further including a third resistance means operatively associated with said piercing pin and said guide channel, said third resistance means acting in conjunction with said first resistance means to position one of said piercing pin points away from said pierceable stopper.

8. The additive transfer device as defined in claim 7 wherein said third resistance means is defined by a groove on said piercing pin and a substantially annular projection extending inwardly into said guide channel.

9. The additive transfer device as defined in claim 1 further including additional sealing means positioned between said hood member and said stopper shoulder defined by a flexible member accommodated in said shoulder and a substantially annular flange extending from said hood member and contacting said flexible member.

10. An improved additive transfer device for storing and transferring a fluid material to a solution container having an exposed stopper, comprising:

an additive container for storing the fluid material, said additive container having a substantially rigid neck portion defining a first and second finish and an opening therethrough;

a pierceable stopper having a shoulder for resting against said second finish of said neck and positioned to close said opening in said additive container neck portion, said pierceable stopper including a guide channel;

a piercing pin having a point on each end, and a passageway therethrough for the flow of the fluid material said piercing pin being slidably positioned within said guide channel;

first and second resistance means comprising spaced-apart projections extending from said piercing pin and at least one annulus extending into said guide channel to position one of said piercing pin points away from said pierceable stopper in one position and to permit passage of said piercing pin point through said pierceable stopper in another position; and a hood member having a flange portion to sealably contact both said container first finish and said shoulder of said pierceable stopper;

whereby a fluid pathway is provided between the containers to permit the fluid material within said additive container to be transferred into the solution container when said piercing pin pierces said pierceable stopper.

11. The additive transfer device as defined in claim 10 wherein said pierceable stopper includes a diaphragm positioned at one end of said guide channel adjacent said additive container opening.

12. The additive transfer device as defined in claim 10 wherein said additive container includes a substantially transverse ledge portion between said container opening and said container second finish and said pierceable stopper includes a complementary ledge portion engaging said container ledge portion.

13. The additive transfer device as defined in claim 12 wherein said guide channel is defined by an outwardly extending tubular member.

14. The additive transfer device as defined in claim 12 further including a weakened portion in said hood member constructed and arranged for removal of a portion of said hood member.

15. The additive transfer device as defined in claim 14 wherein said hood member is fabricated from a thermoplastic resinous material.

16. A three piece stopper system for an additive container having a substantially rigid neck portion defining a finish and an opening therethrough and used for storing and transferring a fluid material comprising:

a pierceable stopper having a shoulder for resting against the finish of the additive container neck and positioned to close said opening therein, said pierceable stopper including a guide channel;

a piercing pin having a point on each end, and a passageway therethrough for the flow of said fluid material said piercing pin being slidably positioned within said guide channel;

first and second resistance means comprising spaced-apart projections extending from said piercing pin and at least one annulus extending into said guide channel to position one of said piercing pin points away from said pierceable stopper in one position and to permit passage of said point through said pierceable stopper in another position; and a hood member having a flange portion to sealably contact said shoulder of said pierceable stopper;

whereby a fluid pathway is provided into the additive container to permit the fluid material within the additive container to transfer therefrom when said piercing pin pierces said pierceable stopper.

17. The three-piece stopper system as defined in claim 16 wherein said pierceable stoper and said hood member include complementary and engageable threads.

18. The three-piece stopper system as defined in claim 16 wherein said hood member includes a weakened portion for removal thereof.

19. The three-piece stopper system as defined in claim 18 wherein said hood is formed from a thermoplastic material.

20. The three-piece stopper system as defined in claim 16 wherein said hood member includes a tear strip for removal thereof.

* * * * *

UNITED STATES PATENT AND TRADEMARK OFFICE

CERTIFICATE OF CORRECTION

PATENT NO. : 4,624,667

DATED : November 25, 1986

INVENTOR(S) : Sangvorn Rutnarak

It is certified that error appears in the above—identified patent and that said Letters Patent is hereby corrected as shown below:

Column 5, line 56 "onto" should read --into--
Column 8, line 13 "stoper" should read --stopper--

Signed and Sealed this

Seventh Day of April, 1987

*Attest:*

DONALD J. QUIGG

*Attesting Officer* *Commissioner of Patents and Trademarks*